United States Patent
Pershing et al.

(10) Patent No.: US 8,583,216 B2
(45) Date of Patent: Nov. 12, 2013

(54) SKIN TYPE ASSESSMENT AND NEVI SCREENING FOR SKIN CANCER WITH A NONINVASIVE, PORTABLE REFLECTANCE SPECTROPHOTOMETER

(75) Inventors: Lynn K. Pershing, Salt Lake City, UT (US); Sancy A. Leachman, Park City, UT (US); Laurence J. Meyer, Holliday, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1134 days.

(21) Appl. No.: 11/115,646

(22) Filed: Apr. 27, 2005

(65) Prior Publication Data

US 2006/0020183 A1 Jan. 26, 2006

Related U.S. Application Data

(60) Provisional application No. 60/568,807, filed on May 6, 2004, provisional application No. 60/565,689, filed on Apr. 27, 2004.

(51) Int. Cl.
*A61B 6/00* (2006.01)
*A61B 5/00* (2006.01)
*G01J 3/40* (2006.01)
*G01J 3/28* (2006.01)

(52) U.S. Cl.
USPC ........... 600/476; 600/477; 600/306; 356/303; 356/326

(58) Field of Classification Search
USPC ........... 600/476, 306, 477; 250/372; 356/303, 356/326
See application file for complete search history.

(56) References Cited

U.S. PATENT DOCUMENTS

| | | | | |
|---|---|---|---|---|
| 4,894,547 A | * | 1/1990 | Leffell et al. | 250/461.2 |
| 5,833,612 A | * | 11/1998 | Eckhouse et al. | 600/476 |
| 6,008,889 A | * | 12/1999 | Zeng et al. | 356/73 |
| 6,058,352 A | * | 5/2000 | Lu et al. | 702/28 |
| 6,907,193 B2 | * | 6/2005 | Kollias et al. | 396/4 |
| 7,029,469 B2 | * | 4/2006 | Vasily | 606/9 |
| 2004/0039379 A1 | * | 2/2004 | Viator et al. | 606/9 |

* cited by examiner

*Primary Examiner* — Long V. Le
*Assistant Examiner* — Katherine Fernandez
(74) *Attorney, Agent, or Firm* — Ballard Spahr LLP

(57) ABSTRACT

The invention relates to a method for objectively measuring skin phototype by reflectance spectrophotometry. The improved method correlates well with clinician-based assessments and is non-invasive, rapid and accurate.

24 Claims, 4 Drawing Sheets

SKIN TYPE ASSESSMENT AND NEVI SCREENING FOR SKIN CANCER WITH A NONINVASIVE, PORTABLE REFLECTANCE SPECTROPHOTOMETER

CROSS-REFERENCE TO RELATED APPLICATIONS

This application claims the benefit under 35 U.S.C. §119 of U.S. Provisional Application Nos. 60/568,807, filed May 6, 2004, and 60/565,689, filed Apr. 27, 2004, the entirety of each of which is incorporated by reference.

TECHNICAL FIELD

The invention relates to biotechnology generally, and more particularly to a method and apparatus for measuring pigmentation of human skin.

BACKGROUND

Human skin pigmentation is important in determining susceptibility to skin cancer. It is a clinically obvious human trait, but very difficult to quantify accurately. Factors affecting skin color include hydration of the stratum corneum, blood flow, hemoglobin oxygenation and melanin. The amount of melanin, its pattern of distribution, the relative amount of the different melanins, pheomelanin and eumelanin all contribute to skin color.

Skin phototype is typically assessed subjectively by self assessment or a trained clinician using sun-exposed (SE) and sun-protected (SP) skin sites as well as hair and eye color, ethnicity, tan response and burn response according to Fitzpatrick Skin Type criteria (FST I-VI). Skin phototype is often used as a normalizing parameter in clinical studies as the basis for risk assessment for skin cancers; high risk=FST I, low risk=FST VI.

Phototype assessment has generally relied on self-assessment by the individual or clinician assessment using a variety of subjective parameters, including hair color, eye color, the number of freckles, tan response, burn response, and number of sunburns after 20 yrs of age. Both professional and self-assessment typically underestimate skin type, particularly those skin types most vulnerable to skin damage (e.g., photo damage), thus exposing the subject to a greater risk of disease (e.g. melanoma skin cancer) induced by improper protective care or by certain high risk activities (e.g., sun bathing). Determination of the type of melanin and quantification of melanin has typically required biopsy and HPLC analysis, which require expensive equipment and specialized training. In addition, these procedures are very time consuming.

Assessing phototype by subjective observation alone is problematic because of interoberserver variance. The disparity between the self-assessment vs. clinician-assessment of skin phototype poses further problems in phototyping.

Self- and Clinician-Assessed Skin Phototype Criteria:

| Skin PhotoType | Skin Color | Sun burn response | Sun tan response |
|---|---|---|---|
| I | White | Always & easily | Never |
| II | White | Always | Minimal & with difficulty |
| III | White | Minimal | Gradual & uniformly light |
| IV | Light Brown | Minimal | Always & Mod. brown |
| V | Brown | Rare | Profuse & Dark brown |
| VI | Black | Never | Maximal & Black |

There is a need for the study of skin type by non-invasive methods. For example, there is a need for an objective reflectance spectrophotometer method to determine skin phototype. Known techniques, such as known methods of reflectance measurements, are not sufficiently sensitive, accurate and/or reproducible enough for some purposes. More sensitive and objective techniques are needed, for example, to study the risk association between skin phototype and incidence of basal cell carcinoma, squamous cell carcinoma and melanoma. More sensitive objective techniques are also needed to quantify the changes in pigmentation over a long period of time and would be particularly useful in the study of pigmented nevi (i.e., moles), especially as they relate to the subsequent development of melanoma skin cancer.

SUMMARY OF THE INVENTION

The invention relates to a method and apparatus for measuring pigmentation of human skin, which is non-invasive, rapid and provides quantitative results. In an exemplary embodiment, the invention relates to an objective measure of skin phototype by reflectance spectrophotometry.

The invention also relates to a method and apparatus for measuring skin pigmentation and changes in skin pigmentation, in vivo, by evaluating reflected spectra.

An exemplary embodiment, provides a method of assessing human skin type by measuring the area under the 450-615 nm interval of the 300-900 nm reflected visible light spectrum, using a noninvasive, hand held reflectance spectrophotometer (e.g., Ocean Optics, FL) to assess skin phototype from a sun-protected region on a subject, such as a human. In another exemplary embodiment, the sun-protected region is the upper, inner arm of a human subject.

In an exemplary embodiment, the methods of the invention may be used to differentiate between benign and atypical nevi (moles).

DETAILED DESCRIPTION OF THE INVENTION

The invention relates to an objective measure of skin phototype by reflectance spectrophotometry. The invention provides an improved method that correlates well with clinician-based assessments.

As used herein, "about" means reasonably close to, a little more or less than the stated number or amount or approximately.

As used herein and in the appended claims, the singular forms "a", "an", and "the" include the plural, unless the context clearly dictates otherwise. For example, reference to "receiving reflected light energy" includes receiving a plurality of reflected light energy, including receiving from one or more measurements and/or sources.

Data from 279 healthy and 101 familial melanoma subjects demonstrate that the area under the reflected intensity (AUIC) from the 450-615 nm wavelength interval (AUIC 450-615 nm) correlates well with six different dermatologist-assessed skin types; high AUIC 450-615 nm values are associated with type I skin types while low AUIC 450-615 nm values are associated with type VI skin types.

The invention provides a method of using reflectance spectrophotometer (RS) data, which correlates well with dermatopathologist-confirmed histology from punch biopsies of the same normal control and nevi (mole). Error in identifying Type I and Type II Nevi, using the method of the invention, is similar to the subjective physician assessment, relative to dermatopathologist-assessed histology.

Figure 1:
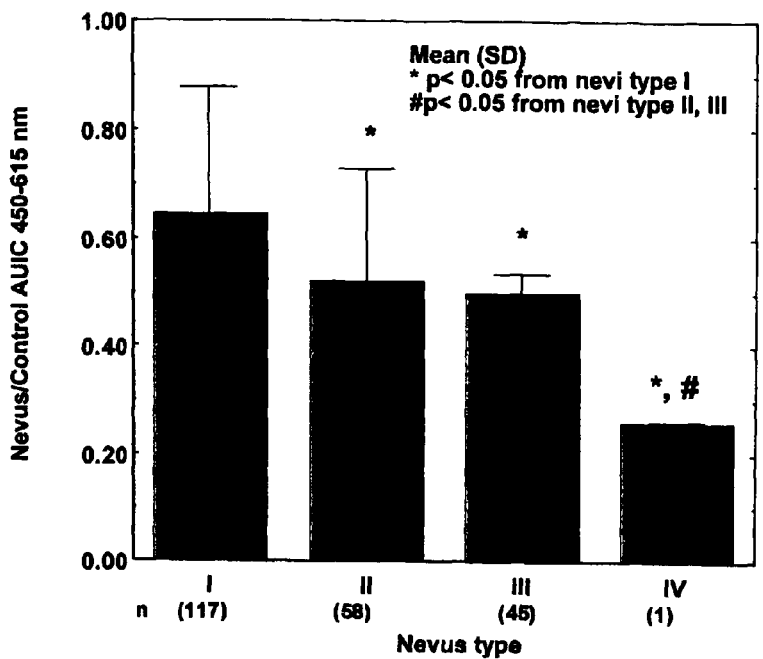
FIG. 1 shows the AUIC 450-615 nm for nevus of types I through IV.
Figure 2:
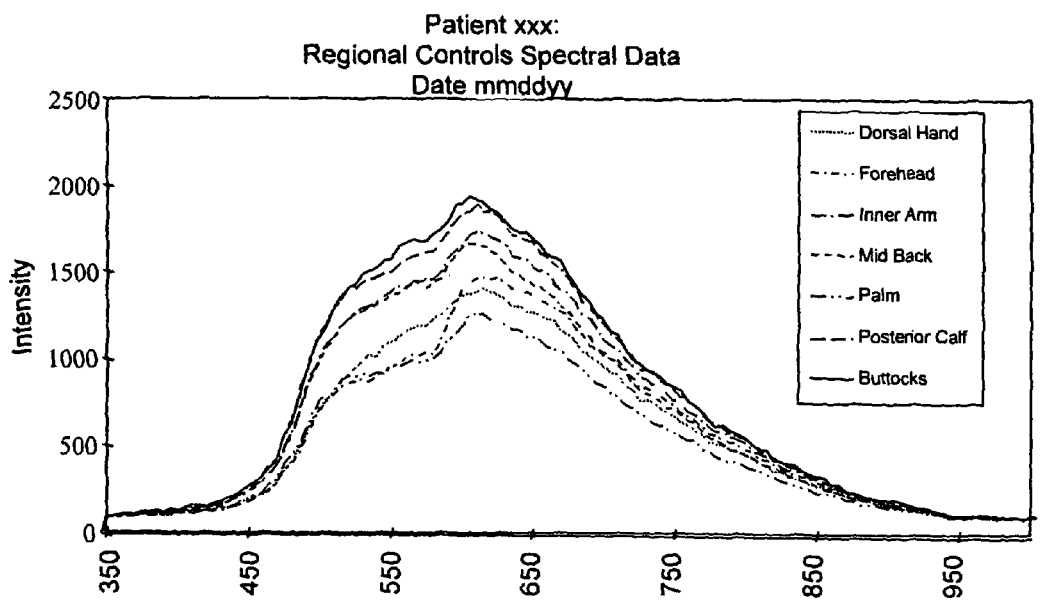
FIG. 2 shows data from a full spectrum analysis.

In an exemplary embodiment, the method uses reflectance spectrophotometer 450-615 nm values from both the nevi and surrounding normal healthy skin, located about 1 cm away from the nevi, to calculate nevi/control value (see, FIG. 1). Data demonstrated that the nevi/control values statistically ($p<0.05$ paired t test) differentiate between normal, benign (Type 0 nevi: non-nevus pigmented skin lesions, Type I nevi: benign nevi including compound, dermal, intradermal congenital and junctional incipiens) and atypical nevi (Type II nevi: atypical nevi with architectural disorder including compound, junctional, halo and congenital nevi, Type III nevi: atypical nevi including dysplastic, compound and junctional nevi, Type IV nevi: severely dysplastic nevi or melanoma in situ and Type V nevi: invasive melanoma) (FIG. 1). Decreasing nevi/control values are associated with increasingly more severe atypical, cancerous-type nevi (FIG. 1). This method is not influenced by inherent skin color, as the calculation of the nevi/control ratio corrects for the inherent skin color at the nevi location. Data was generated from normal surrounding skin for each nevus from 197 nevi from patients at the Tom C Mathews, Jr. Familial Melanoma Research Clinic at Huntsman Cancer Institute.

The invention provides a safe, rapid, objective, more discriminating, and inexpensive method of measuring pigmentation, which does not require complete disrobing or subjective assessment of tanning/burning response to demographics questionnaires, is independent of hair color, eye color, and time of year (low temporal variability), and not influenced by race or ethnic category. Furthermore, the method is fast, each instrument reading requires about 10 sec, and skin phototype assessment requires about 1 to about 2 minutes.

Differential nevi screening according to the invention, provides a safe, rapid, objective, noninvasive, and inexpensive screen, that does not require a physician office visit. The method is also fast, in that each instrument reading requires about 10 sec and differential nevi status requires about 2 minutes per nevi. The invention also provides an elegantly simple method to objectively assess skin phototype.

Reflectance has been measured using the full visible light spectrum (300-900 nm), the present invention surprisingly demonstrates that the spectral interval between about 450 nm and about 615 nm provides an improved method of analyzing the skin of a subject. Objective quantification of skin phototype has also been investigated with colorimeters, using filters to determine the intensity of reflected light over broad regions of the color spectrum.

Baseline pigmentation may be assessed by measuring reflectance spectrum from a sun-protected region, such as the upper inner arm. Normalization using vitiligo skin was not required to correct for components of skin color due to hydration, keratin, blood flow and hemoglobin oxygenation.

Likewise, inducible pigmentation may be assessed by subtracting data obtained from a sun-exposed (or other induced pigmentation site), such as a dorsal forearm, from that of a sun-protected region (or non-induced pigmentation site), such as the upper inner arm. Thus, allowing each person or subject to serve as its own control.

Sun-exposed skin regions include, but are not limited to, the forehead, face, shoulders, temple, dorsal hands and dorsal forearms of subjects, while sun-protected regions typically include, but are not limited to, skin in the inner upper arm (for example, about 4-5 cm dorsal to the center of the armpit region) region or buttocks region. These different locations represent variation in epidermal, dermal and subcutaneous thickness.

Any display known in the art may be used for observing the spectral waveforms, for example, a CRT, LCD or plasma display. Any computer software program known in the art may be used to evaluate the reflectance data. For example, 16 bit software may be used, preferably, 32 bit software, which provides 4× more sensitivity in measurements, may be used. Such computer software may be used to digitize the reflectance intensity of the spectrum. Any spectrometer or colorimeter known in the art, which generates a reflectance spectrum from between about 450 to about 615 nm, may be used in the invention. A non-exclusive list of spectrometers, which may be used in the invention, includes, but is not limited to, the S2000 Fiber Optic Spectrometer and HR2000 High Resolution Spectrometer from Ocean Optics, Inc.

In an exemplary embodiment, the method uses only a sun-protected skin site, for example, on the upper inner arm to assess skin type. Such an embodiment provides an advantage due to the seasonal variance observed at sun-exposed skin sites (17% CV for a skin type II individual), which may reduce the reliablity for skin phototyping. In another exemplary embodiment, both a sun-exposed site and a sun-protected site are used to assess skin phototype, preferably reflectance is measured using the spectral interval from about 450 and about 615 nm.

In another exemplary embodiment, a best-mathematical fitting program (MATLAB®) is used to fit the reflectance AUIC data from the 450-615 nm spectral interval from a sun-protect (SP) skin site (inner upper arm). The invention provides a mathematical equation (quadratic equation) to describe the association between reflectance and skin type, which statistically differentiates between skin types. Thus, the invention provides a means for modifying the output of a reflectance measurement as a skin type value, which may be displayed to an end user.

In another exemplary embodiment, the method and/or system of the invention may be adapted as a portable device, for example, with a portable CPU containing device, such as a laptop computer, along with a spreadsheet calculation and/or macro to back-calculate skin type from AUIC 450-615 nm, for example, calculated in a EXCEL® or Lotus 1-2-3 or QUATTRO PRO® spreadsheet. Optionally, reflectance intensity may be selected at 5 nm intervals for the calculation of AUIC 450-615 nm and assessment of skin type. As will be recognized by a person of ordinary skill in the art, in light of the present disclosure, reflectance intensities at intervals greater than or less than 5 nm may be used to calculate skin type, as appropriate and desirable for the speed (e.g., computational speed of a computer) and/or accuracy of the desired assessment. Optionally, such a laptop may be provided with an independent battery backup and/or independent backup power supply.

In an exemplary embodiment, the distal end of a fiberoptic probe may be positioned in direct contact with the skin (nevi) surface, preferably, perpendicular to the skin (nevi) surface. However, other distances and/or angles may be appropriate. As will be recognized by a person of skill in the art, ambient light that enters the reflectance probe should be accounted for. In an exemplary embodiment, measurement of reflectance is conducted in an environment having reduced ambient light. In another exemplary embodiment, an Ocean Optics S2000 Fiber Optic Spectrometer instrument is used in an environment that is maintained at a temperature of about 23±2° C.

An exemplary embodiment of the invention employs a ratio of a subject's sun-exposed skin to his (or her) own non-sun-exposed skin, thus, the subject acts as his (or her) own control and the subject-to-subject level variations are eliminated or reduced.

The present invention may also be used to detect variations in degree of pigmentation from site to site, or neighboring sites within a very close area. The method of the invention also has applications in the pharmaceutical industry for a means of testing new products thought to have an effect on the reversal of photoaging and/or skin damage. Current technology involves the use of plaster casts of skin and the visual evaluation of surface photodamage (wrinkles). The quantitative method of measuring photoaging should prove valuable for this purpose, as well as for the evaluation of other products related to skin aging. Likewise, the invention may be used to test the protective effects of products such as sun screens.

In an appearance-conscious society, the method and apparatus of the present invention may have widespread appeal in a non-medical setting, specifically, the method may be used as a non-invasive procedure in commercial and cosmetic treatment centers which might be interested in measurement of skin pigmentation to enhance their service to clients as part of a cosmetic or therapeutic regimen. Improvement in skin, relating to treatment, could be documented and recorded for the patient's benefit using the inventive method.

The invention provides a rapid, inexpensive method of accurately determining skin type that may be beneficially used, for example, in a cosmetic section of a store to customize product selection for a customer. In an exemplary embodiment, a station, such as a Kiosk, may be established to read skin reflectance. In addition, a cosmetics manufacturer may use the invention in the process of designing appropriate products. The invention may show before and after differences, due to face exfoliation or some other skin treatment. Because of the speed, lack of expensive equipment and/or accuracy of the invention, a store may include, a department store, a cosmetics specialty store, and/or traveling sales people (for example, Mary Kay, NuSkin, Avon and/or sales people associated therewith).

The invention is further shown by way of the following illustrative examples.

Example I

Evaluation of skin phototype using the reflectance spectrophotometer in 279 healthy subjects and 101 patients from a familial melanoma research clinic (FMRC), all age 18-72 yrs old from varied racial and ethnic backgrounds, was conducted.

Figure 3:
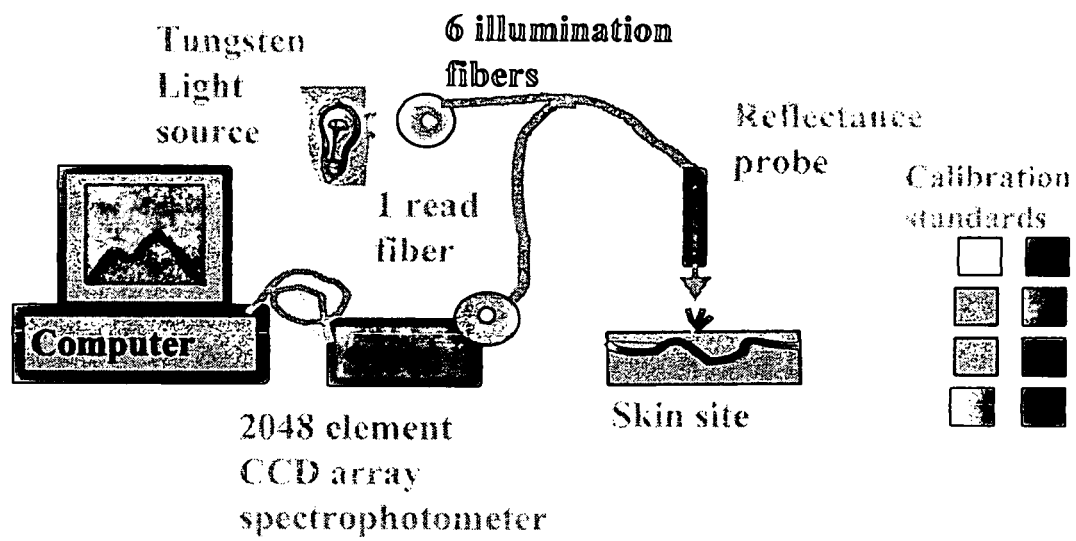
FIG. 3 illustrates the use of an Ocean Optics S2000 spectrophotometer in the method of the invention.

Reflectance Spectrophotometer (RS): An Ocean Optics S2000 (software OOI v 1.0.1.3), which utilizes a tungsten light source with 6 illumination fibers, a single fiber optic spectrometer with a grating of 600 lines blazed at 500 nm and bandwidth 350-1000 nm was used to record spectrophotometeric measurements. The instrument was calibrated with commercial color and light/dark standards. FIG. 3 illustrates the use of an Ocean Optics S2000 spectrophotometer in the method of the invention.

Reading location consisted on a sun protected (SP) site, which was the right inner upper arm, and a sun exposed (SE) site, which was the right dorsal forearm 3 cm above the wrist.

RS-assessed skin phototype: Calculated as the area under the reflected light Intensity (AUIC) over a spectral range of about 450 nm to about 615 nm with the trapezoidal rule:

$$\Sigma 0.5*[(nm615-nm450)*(I615+I450)]$$

RS-fitted skin phototype fitted using the AUIC 450-615 nm values, analyzed with MATLAB® computer software.

Example II

Figure 4:
FIG. 4 illustrates SP and SE AUIC as a function of subjective skin phototype.

SP and SE AUIC decrease proportionately as a function of increasing skin phototype. In addition, both SP and SE could be used for differentiating skin phototype (see, FIG. 4).

Figure 5:
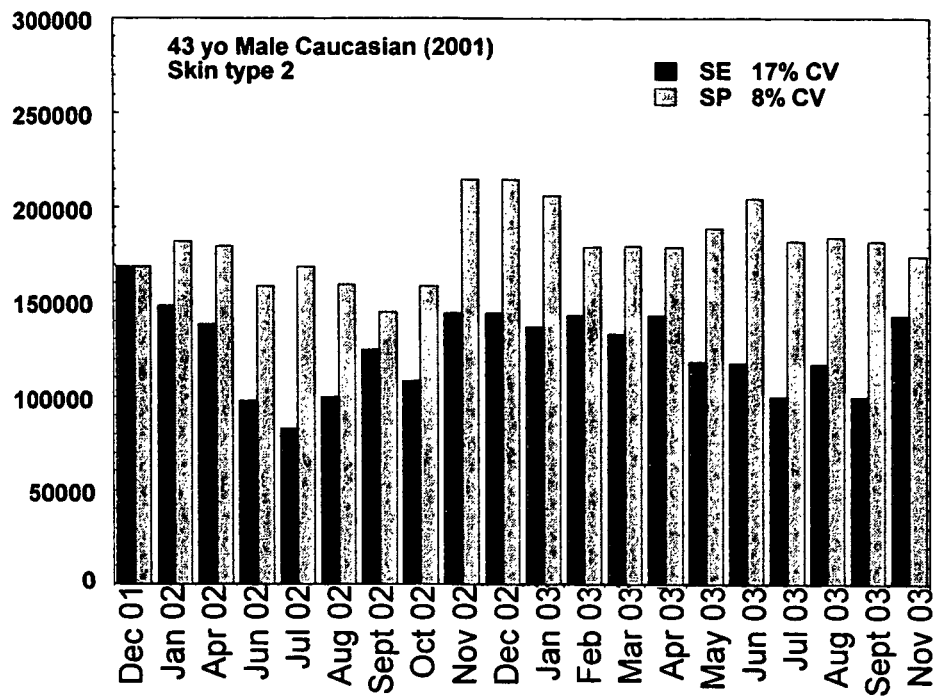
FIG. 5 illustrates the temporal variability of SP vs. SE AUIC.

SE AUIC is dependent on the time of year, being greater in the Winter, and smaller in Summer. In contrast, SP AUIC is independent of the time of the year (8% CV), and provides a consistent temporal site for skin phototype determination (see, FIG. 5).

Example III

The RS instrument is highly reproducible for skin phototype assessment. Multiple measurements of the SP Inner Arm site (Within-site) has a low 5% CV. Measurement of multiple sites in the SP inner arm region (between-site, same region) has an 8% CV (see, Table 1).

TABLE 1

| reproducibility for skin phototype assessment. | |
| --- | --- |
| Variability parameter | % CV |
| Within-site SP inner arm | 5% |
| Between-site, same region on the SP inner arm | 8% |

Example IV

Figure 6:
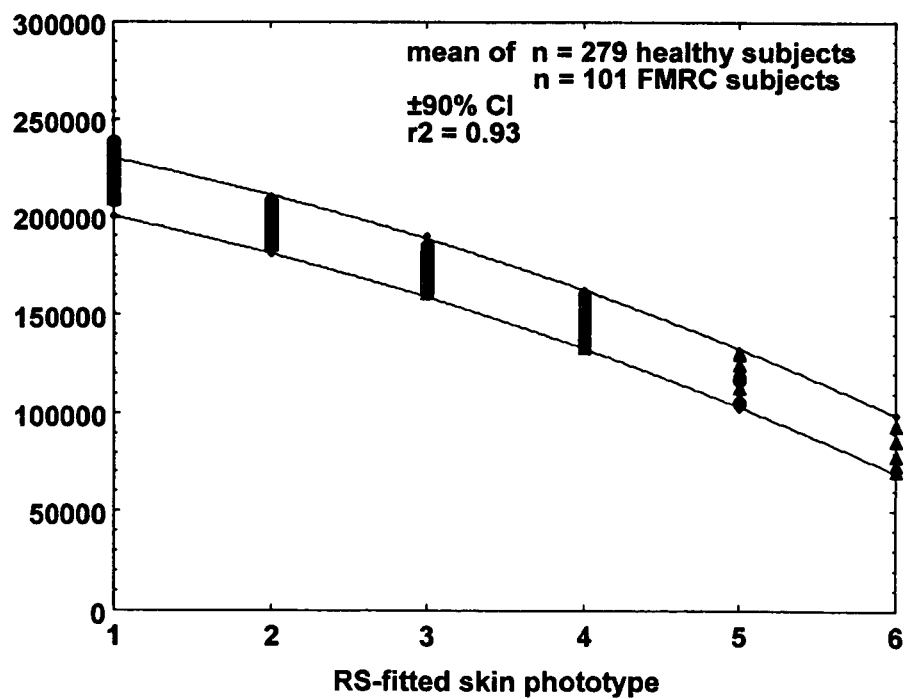
FIG. 6 shows that skin phototype is a quadratic function of the reflectance spectrophotometer (RS)-measured and MATLAB®-fitted values of sun-protected skin over the 450-615 nm reflected spectral interval.

Skin typing 279 healthy and 101 FMRC subjects using an exemplary method of the invention, as illustrated in Example I, fit a quadratic equation ($r2=0.93$) with 90% confidence intervals that statistically differentiates between each of skin of types 1-6 (see, FIG. 6).

Example V

Figure 7:
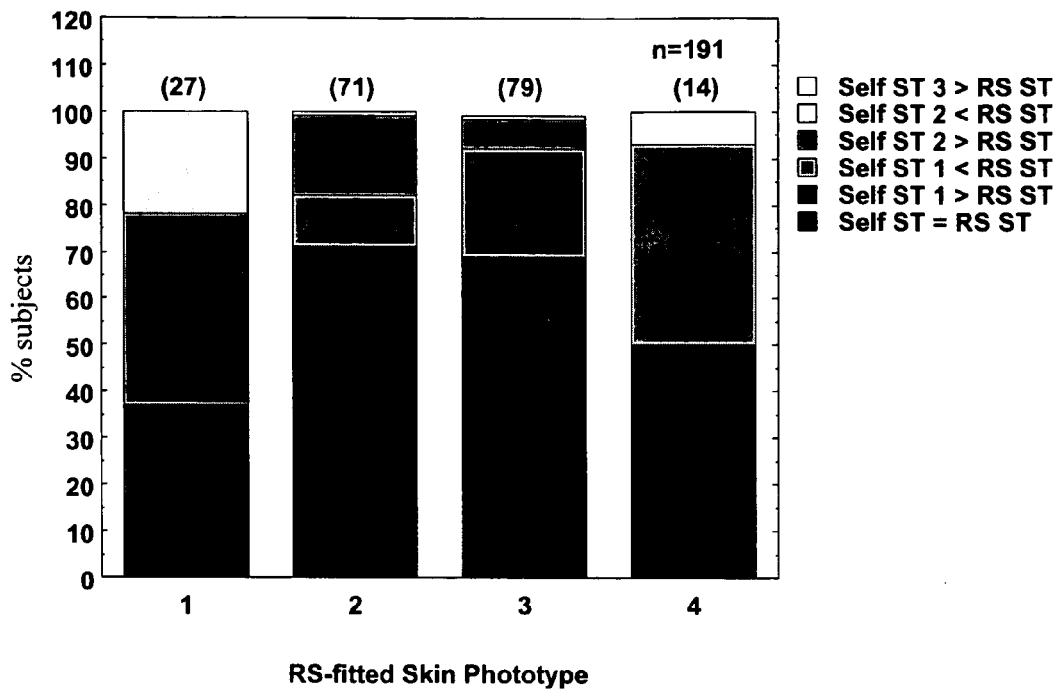
FIG. 7 illustrates the accuracy of Self-assessed vs. RS-fitted Skin Phototypes.

Self-assessed vs. instrument-measured according to the invention skin phototype agrees (black) or is ±1 different (blue+cyano) in 80-95% subjects of skin types 2-4, but agree only 35% in skin type 1 (see, FIG. 7). Thus, subjects having skin phototype 1, under estimate their skin type more than other skin phototypes.

Figure 8:
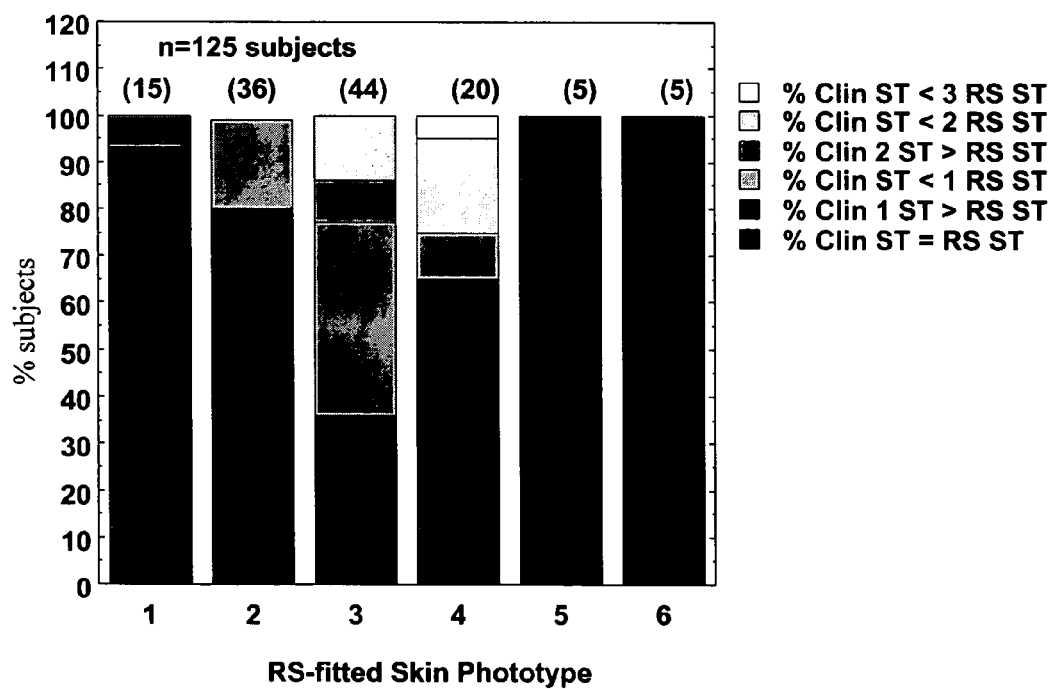
FIG. 8 illustrates the accuracy of Clinician-assessed vs. RS-fitted Skin Phototypes.

Clinician-assessed vs. instrument-measured, according to the method of the invention, skin phototype agrees (black) or is ±1 different (+1=blue and −1=cyano) in 90-100% subjects of skin types 1, 2, 5 and 6, and 75% in skin types 3 and 4 (FIG. 8). Clinicians assessed skin phototype better than the individual, but still tend to underestimate skin phototype 1 (I).

In one exemplary embodiment of the invention, the reflectance spectrophotometer measure of the sun-protected, upper, inner arm provides a rapid, easily accessible, noninvasive, reproducible and accurate method to objectively determine skin phototype. Clinician-assessment agreed better with instrument-measured skin phototype than self-assessment, but both subjective methods tended to underestimate skin phototype 1, which is more highly associated with skin cancer risk.

All references, including publications, patents, and patent applications, cited herein are hereby incorporated by reference to the same extent as if each reference were individually and specifically indicated to be incorporated by reference and were set forth in its entirety herein.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for measuring and quantifying skin phototype of a subject, said method comprising:
   providing a tungsten light energy source having a known intensity;
   directing the light energy to an untreated sun-protected skin area on a subject;
   receiving reflected light consisting of light energy over the entire light spectrum interval from about 450 nm to about 615 nm from the untreated sun-protected skin area;
   performing a reflectance spectral analysis of said received reflected light energy; and
   developing a numerical value representative of pigmentation in the untreated skin area based on an area under the reflectance spectral analysis.

2. The method according to claim 1, wherein providing the light energy source and receiving reflected light energy comprises using a spectrometer.

3. The method according to claim 2, wherein the spectrometer generates a reflectance spectrum from between about 450 nm to about 615 nm.

4. The method according to claim 1, wherein directing the light energy source to the untreated sun-protected skin area comprises a fiberoptic path.

5. The method of claim 4, wherein the fiberoptic path includes a distal end of an instrument probe, the method including arranging the distal end to be in contact with, and perpendicular to, the sun-protected untreated skin area.

6. The method according to claim 1, wherein performing a spectral analysis of said received light energy comprises using a spreadsheet.

7. The method according to claim 1, wherein performing a spectral analysis of said received reflected light energy and developing a numerical value representative of pigmentation in the untreated sun-protected skin area comprise using a portable CPU containing device.

8. The method according to claim 1, further comprising providing an analysis station.

9. The method according to claim 8, wherein the analysis station is a kiosk.

10. The method according to claim 8, further comprising providing instructions regarding how to direct the light energy to the untreated sun-protected skin area.

11. The method according to claim 1, further comprising displaying the intensity of the reflected light energy.

12. The method according to claim 1, wherein developing a numerical value representative of pigmentation in the untreated sun-protected skin area comprises displaying a representation of skin phototype for the subject.

13. The method according to claim 12, wherein the subject is a mammal.

14. The method according to claim 13, wherein the untreated sun-protected skin area is the upper, inner arm.

15. The method according to claim 14, wherein the skin phototype for the subject is displayed according to a Fitzpatrick skin type criteria.

16. The method of claim 1, comprising receiving reflected light energy from the sun-protected untreated skin area by a fiberoptic path.

17. A method for quantifying and evaluating skin pigmentation of a human subject, the method comprising:
   exposing a first sun-protected skin area of a human subject to a tungsten light energy source of a predetermined intensity;
   exposing a second skin area of the human subject to the light energy source, wherein the second skin area is thought to have a condition affecting pigmentation;
   sensing spectra of the reflected light energy from both the first sun-protected skin area and second skin area;
   obtaining a measure of intensity of the reflected light energy from both the first sun-protected skin area and second skin area consisting of light energy spectra over a range of about 450 nm to about 615 nm;
   comparing the measure of intensity for the first sun-protected skin area to the measure of intensity for the second skin area; and
   evaluating the condition of the second skin area based on the comparison of the measure of intensity of the first sun-protected and second skin areas.

18. The method of claim 17, comprising exposing the first sun-protected skin area to light energy for a limited time period less than 5 sec.

19. The method according to claim 17, comprising analyzing the intensity with a computer spreadsheet program.

20. The method according to claim 19, comprising using a portable CPU containing device.

21. The method according to claim 20, wherein the portable CPU containing device is a laptop computer.

22. The method according to claim 17, wherein the condition affecting pigmentation is a nevus.

23. The method according to claim 22, comprising evaluating the nevus as benign or atypical.

24. The method according to claim 17, comprising analyzing the intensity with a high-level technical computing language and interactive environment for algorithm development, data visualization, data analysis, and numeric computation.

* * * * *